United States Patent [19]

Carruth et al.

[11] Patent Number: Plant 6,670

[45] Date of Patent: Mar. 14, 1989

[54] FLORIBUNDA ROSE PLANT CV. AROREAS

[75] Inventors: Thomas F. Carruth, Canoga Park; Jack E. Christensen, Ontario, both of Calif.

[73] Assignee: Armstrong Roses, Somis, Calif.

[21] Appl. No.: 67,622

[22] Filed: Jun. 26, 1987

[51] Int. Cl.[4] ..... A01H 5/00

[52] U.S. Cl. ..... Plt./29

[58] Field of Search ..... Plt./29

*Primary Examiner*—Robert E. Bagwill

*Attorney, Agent, or Firm*—Majestic, Gallagher, Parsons & Siebert

[57] ABSTRACT

This invention relates to a new and distinct variety of floribunda rose plant cv. Aroresas, particularly suited for cut flowers, identified by its abundant production of long, strong, thornless stems bearing uniform deep red buds.

1 Drawing Sheet

The present invention relates to a new and distinct variety (cv. Aroresas) of rose plant of the floribunda class. The plant is a tall, greenhouse seedling of the upright type, with long stems, and very few prickles, cultivated for cut flowers. Its hardiness is yet untested. It was first originated by Thomas F. Carruth and Jack E. Christensen in Ontario, Calif.; U.S.A. under conditions of careful control and observation, and has as its seed parent the hybrid tea rose, Red Success and as its pollen parent, the rose Mary Devor.

The new rose cv. Aroresas is particularly distinguishable from other commercialized rose cultivars by the following combination of characteristics: its upright growing habit and long, flower-bearing stems with very few prickles; and it well-formed and relatively small (approximately 1¼ to 1½ inches in diameter) deep red colored blossoms, essentially as described and illustrated herein.

Aroresas holds its distinguishing characteristics through succeeding propagations by cuttings and budding and in vitro propagation.

The new variety cv. Aroresas may be distinguished from its seed parent, Red Success by the following combination of characteristics: Whereas Red Success is a hybrid tea rose, Aroresas is a floribunda rose of the sweetheart type. The flower color of Aroresas is a deep dark red whereas the flower color of Red Success is an orange-red. Aroresas has very few prickles on its branches and trunk whereas Red Success has a moderate number of prickles on its branches and its trunk.

The new variety may be distinguished from its pollen parent, Mary Devor by the following combination of characteristics: Aroresas has very few prickles on its branches and trunk whereas Mary Devor bears a moderate number of prickles on its branches and trunk. The buds of the new variety are greater in size than the buds of Mary Devor.

The accompanying drawing illustrates the new variety in color as grown in Somis, Calif., and shows the flowering thereof from bud to full bloom.

The descriptive matter which follows pertains to roses of the new variety grown in the greenhouse in Somis, Calif., and is believed generally to apply to similar conditions elsewhere. Plants and flowers of the new variety grown in other locations may vary in slight detail according to the climatic, soil and cultural conditions under which the variety is grown.

Throughout this specification, color names beginning with a small letter signify that the name of that color as used in common speech is aptly descriptive. Color names beginning with a capital letter designate values based upon the R.H.S. Colour Chart of The Royal Horticultural Society of London, England.

FLOWER

The new variety usually bears its flowers singly, sometimes two to three to a stem. Flowers are borne on strong stems that are long for the class. In the greenhouse, the plant blooms very abundantly and nearly continuously during the growing season. Blooms have a slight fragrance.

BUD

The peduncle is of average length for the class, of average to heavy caliper, strong and erect. The peduncle is usually smooth with few stipitate glands. Bud color is near Green 141C.

Before the calyx breaks, the bud is medium in size for the class, of medium length, ovoid in form with a conspicuous neck. There are foliaceous appendages and stipitate glands on the surface of the bud, with deeply serrate foliaceous parts extending beyond the tip of the bud and equal to three quarters or more of its length.

As the calyx breaks, bud color is between Red 45A and Red 46A.

The inner surface of the sepals bears a fine wooly tomentum. Sepal margins are lined with gland-tipped cilia, stipitate glands and hairs.

As the first petals opens, buds are average in size for the class, of medium length and pointed to ovoid in shape. Color of the outside and inside of the bud petals is a uniform royal red, between Red 45A and Red 46A.

The bud opens well and is not retarded, prevented from opening, or destroyed by hot, wet or dry weather.

BLOOM

The size of the bloom when fully open is average for the class, about 2 inches to about 2.5 inches in diameter. Petalage is double, averaging from about 27 to 30 petals arranged regularly, plus 6 or 8 petaloids. Blooms are high-centered to flat topped and full in form, with spiraled petals. Petal edges are reflexed outward. When fully open, petals are somewhat loosely cupped, the petal edges reflexed outward.

The petals are heavy in substance, of medium thickness, velvety on the inside surface and slightly velvety on the outside surface. Outside petals are oval to nearly round in shape with rounded tips usually bear one notch. Intermediate petals are nearly oval to narrowly obovate with rounded tips and usually bear one notch. Inside petals are nearly oval with rounded tips and usually bear one notch.

The following paragraph describes the color values observed in a newly opened flower from a plant of the new variety grown in a greenhouse in Somis, Calif. in May of 1987.

The outside surface of the outside petals is of uniform color, near Red-Purple 59A. The inside surface of the outside petals is of uniform color, near Greyed-Purple 187B.

The outside and inside surface of the intermediate petal is near Red-Purple 60A. The outside surface of the inner petal is near Red-Purple 60B and the inside surface is near Red-Purple 60A.

The general color effect of the bud and newly opened flowers is a deep royal red. Flowers open for three days maintain the same general color effect of the flower when newly open.

The following paragraph describes the color values observed in a flower open for three days indoors from a plant of the new variety in June, 1987 at Somis, Calif.

The color of the outside and inside surface of both the outside and inside petals is near Red-Purple 60B and Red-Purple 60A, respectively.

Petals usually drop off cleanly and are not particularly affected by hot of dry weather. Flowers on garden plants grown in the month of June last from 3 to 4 days. Cut flowers from rose plants grown in the greenhouse last from 6 to 7 days in May when kept at living room temperatures.

REPRODUCTIVE ORGANS

The many stamens are arranged regularly about the pistils; a few may also be mixed with petaloids. Filaments are medium in length and most have medium sized anthers. Anthers open approximately all at once. Mature anthers are Greyed-Yellow 163A in color; immature anthers are Greyed-Yellow 162A in color. Pollen is produced in abundant quantities and is Greyed-Yellow 163B in color.

Pistils are average in number for the class (about 30). Styles are of average length and are somewhat bunched. Stigma color is near Greyed-Yellow 162C. Ovaries are mostly all enclosed in the calyx with a few protruding therefrom.

Immature hips of the variety are smooth, short and pointed. Hips are near Green 141C in color, with some Orange-Red 31A near the tip.

Sepals are permanent and of medium length. The inside surface of the sepals is near Green 138B in color; the color of the outside sepal surface is near Green 137B.

Few seeds are produced, around 5 to 8 in number.

FOLIAGE

The abundant compound leaves are heavy and glossy and usually comprise 5 to 7 leaflets. Leaflets are oval in shape, with acute apices; their bases are usually obtuse and margins are simply serrate.

The color of the upper leaf surface is Green 147A; the lower leaf surface is near Green 148B. New growth is Green 146A in color, tinged with Greyed-Red 182B on the upper leaf surface. The under surface of young leaves is Greyed-Red 182B with Green 146D beneath the surface.

The rachis is of average size. Its upper side is grooved with some stipitate glands on the edges. The underside is sparsely prickly with stipitate glands.

Stipules are short in length for the class, moderately narrow, and have short points which usually turn out at an angle of less than about 45°.

Plants of the new variety are, on the average, more resistant to mildew than other cultivars now in commerce when grown under comparable conditions at Somis, Calif.

GROWTH

Plants of the new variety are of a tall upright habit, and much branched. Plant growth is very free and vigorous. Canes are of heavy caliper for the class. The main stems are Greyed-Green 191A in color. They bear very few thorns which are short for the class and hooked slightly downward. Thorns are Greyed-Orange 174B in color. The thorn base is short and narrow. There are no prickles or hairs.

Branches are Greyed-Green 191A in color; they bear very few large thorns and these are short for the class. Thorns are hooked downward and have a short and narrow base. Thorns are Greyed-Orange 161B in color. There are no prickles or hairs.

New shoots are Green 143B in color, tinged with Greyed-Red 186B. New shoots bear very few thorns for the class. Thorns are Greyed-Purple 185D at the base and Greyed-Yellow 162 at the tip. There are no small prickles or hairs.

I claim:

1. A new and distinct variety of floribunda rose plant cv. Aroresas and the parts thereof, being particularly characterized by its upright habit; its long, flower-bearing stems with very few prickles; and its long lasting, well formed and relatively small flowers of uniform red color, substantially as described and illustrated herein.

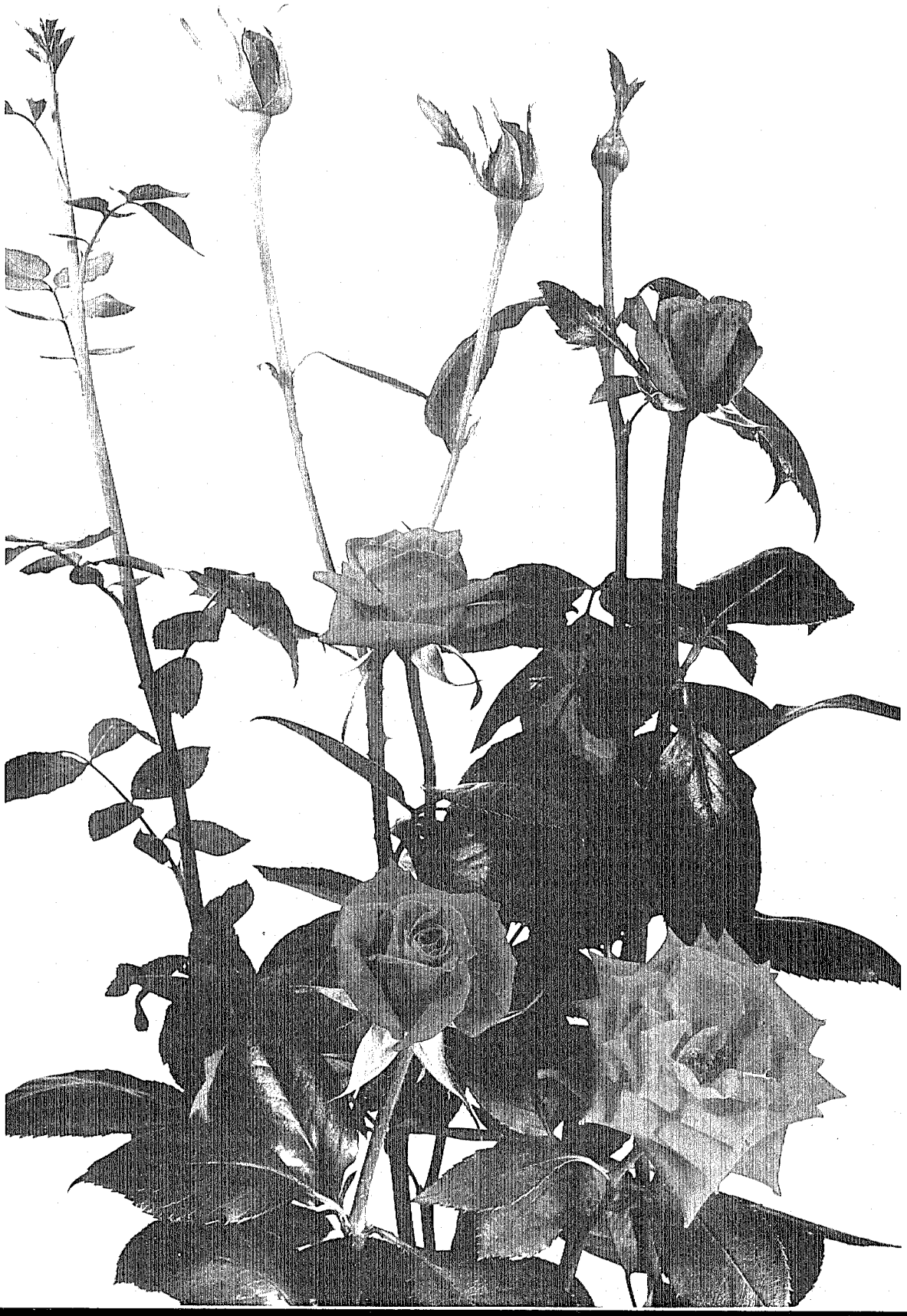

* * * * *